US008962894B2

(12) United States Patent
Allgeier et al.

(10) Patent No.: US 8,962,894 B2
(45) Date of Patent: *Feb. 24, 2015

(54) PROCESS FOR PREPARING 1, 6-HEXANEDIOL

(71) Applicant: E I du Pont de Nemours and Company, Wilmington, DE (US)

(72) Inventors: Alan Martin Allgeier, Wilmington, DE (US); Wathudura Indika Namal De Silva, Wilmington, DE (US); Ekaterini Korovessi, Wilmington, DE (US); Carl Andrew Menning, Newark, DE (US); Joachim C Ritter, Wilmington, DE (US); Sourav Kumar Sengupta, Wilmington, DE (US); Christina S Stauffer, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/729,464

(22) Filed: Dec. 28, 2012

(65) Prior Publication Data

US 2013/0172578 A1 Jul. 4, 2013

Related U.S. Application Data

(60) Provisional application No. 61/582,067, filed on Dec. 30, 2011, provisional application No. 61/639,404, filed on Apr. 27, 2012, provisional application No. 61/639,436, filed on Apr. 27, 2012, provisional application No. 61/639,449, filed on Apr. 27, 2012.

(51) Int. Cl.
*C07C 29/141* (2006.01)
*C07D 309/10* (2006.01)
*C07C 29/145* (2006.01)
*C07D 307/12* (2006.01)
*C07C 29/132* (2006.01)

(52) U.S. Cl.
CPC ............ *C07C 29/145* (2013.01); *C07D 309/10* (2013.01); *C07D 307/12* (2013.01); *C07C 29/132* (2013.01)
USPC ........................................................ 568/862

(58) Field of Classification Search
CPC ............................... C07C 29/141; C07C 45/49
USPC ........................................................ 568/862
See application file for complete search history.

(56) References Cited

U.S. PATENT DOCUMENTS

| | | |
|---|---|---|
| 2,082,025 A | 6/1937 | Peters |
| 2,201,347 A | 5/1940 | Rittmeister |
| 2,440,929 A | 5/1948 | Frederick |
| 2,768,213 A | 10/1956 | Whetstone et al. |
| 3,070,633 A | 12/1962 | Torleif et al. |
| 3,083,236 A | 3/1963 | Utne et al. |
| 3,189,651 A | 6/1965 | Ellery et al. |
| 3,215,742 A | 11/1965 | Horlenko et al. |
| 3,223,714 A | 12/1965 | Manly et al. |
| 3,268,588 A | 8/1966 | Horlenko et al. |
| 3,270,059 A | 8/1966 | Winderl et al. |
| 3,917,707 A | 11/1975 | Williams et al. |
| 3,933,930 A | 1/1976 | Dougherty et al. |
| 4,254,059 A | 3/1981 | Grey |
| 4,400,468 A | 8/1983 | Faber |
| 4,401,823 A | 8/1983 | Arena |
| 4,780,552 A | 10/1988 | Wambach et al. |
| 5,112,994 A | 5/1992 | Koseki et al. |
| 5,210,335 A | 5/1993 | Schuster et al. |
| 5,412,111 A | 5/1995 | Matsumoto et al. |
| 5,538,891 A | 7/1996 | Schneider et al. |
| 5,696,303 A | 12/1997 | Darsow et al. |
| 5,981,769 A | 11/1999 | Baur et al. |
| 6,008,418 A | 12/1999 | Baur et al. |
| 6,087,296 A | 7/2000 | Harper et al. |
| 6,147,208 A | 11/2000 | Achhammer et al. |
| 6,265,602 B1 | 7/2001 | Voit et al. |
| 6,403,845 B1 | 6/2002 | Pfeffinger et al. |
| 6,407,294 B1 | 6/2002 | Breitscheidel et al. |
| 6,433,192 B1 | 8/2002 | Fischer et al. |
| 6,462,220 B1 | 10/2002 | Luyken et al. |
| 6,593,481 B1 | 7/2003 | Manzer |
| 6,818,781 B2 | 11/2004 | Bhatia |
| 7,019,155 B2 | 3/2006 | Manzer |

(Continued)

FOREIGN PATENT DOCUMENTS

| | | |
|---|---|---|
| CA | 2800797 A1 | 12/2011 |
| CN | 101628875 A | 1/2010 |

(Continued)

OTHER PUBLICATIONS

BLANC_2000_GREENCHEMISTRY_89_91.
Buntara etal Angew Chem Int Ed 2011 50 1-6.
Corma 1995 CHEMREV 95 559-614.
Huber Green Chem 2011 13 91.
Huber JournalofCatalysis 270 2010 48-59.pdf.
Huber Journal of Catalysis 279 2011 257-268.pdf.
Jung et al Journal of Organic Chemistry 63 (1998) 8133-8144.
Miftakhov et al Russian Chemical Reviews 63(10) 869-882 (1994).
Ponder Applied Biochemistry and Biotechnology vol. 24/25, 41-47 1990.

(Continued)

*Primary Examiner* — Elvis O Price

(57) ABSTRACT

Disclosed are processes for preparing 1,6-hexanediol and synthetic intermediates useful in the production of 1,6-hexanediol from renewable biosources. In one embodiment, a process comprises contacting levoglucosenone with hydrogen in the presence of a first hydrogenation catalyst at a first temperature to form product mixture (I); and heating product mixture (I) in the presence of hydrogen and a second hydrogenation catalyst at a second temperature to form product mixture (II) which comprises 1,6-hexanediol.

13 Claims, No Drawings

(56) References Cited

U.S. PATENT DOCUMENTS

| | | | |
|---|---|---|---|
| 7,230,145 | B2 | 6/2007 | Kadowaki et al. |
| 8,053,608 | B2 | 11/2011 | Kouno et al. |
| 8,053,615 | B2 | 11/2011 | Cortright et al. |
| 8,501,989 | B2 | 8/2013 | Boussie et al. |
| 8,524,925 | B2 | 9/2013 | Sabesan et al. |
| 8,669,393 | B2 | 3/2014 | Boussie et al. |
| 2003/0212298 | A1 | 11/2003 | Brasse et al. |
| 2006/0014988 | A1 | 1/2006 | Fischer et al. |
| 2007/0287845 | A1 | 12/2007 | Lilga et al. |
| 2008/0200698 | A1 | 8/2008 | Reichert et al. |
| 2009/0156841 | A1 | 6/2009 | Sanborn et al. |
| 2009/0314992 | A1 | 12/2009 | Pinkos et al. |
| 2010/0113841 | A1 | 5/2010 | Suzuki et al. |
| 2010/0216958 | A1 | 8/2010 | Peters et al. |
| 2010/0274030 | A1 | 10/2010 | Bevinakatti et al. |
| 2010/0317822 | A1 | 12/2010 | Boussie et al. |
| 2011/0040131 | A1 | 2/2011 | Kouno et al. |
| 2011/0071306 | A1 | 3/2011 | Robinson |
| 2011/0218318 | A1 | 9/2011 | Boussie et al. |
| 2011/0263916 | A1 | 10/2011 | Bao et al. |
| 2011/0312051 | A1 | 12/2011 | Kalnes et al. |
| 2012/0010419 | A1 | 1/2012 | Pinkos et al. |
| 2012/0022298 | A1 | 1/2012 | Pinkos et al. |
| 2012/0035399 | A1 | 2/2012 | Abillard et al. |
| 2012/0059174 | A1 | 3/2012 | Abillard et al. |
| 2012/0116122 | A1 | 5/2012 | Feist et al. |
| 2012/0172579 | A1 | 7/2012 | Qiao et al. |
| 2013/0172578 | A1 | 7/2013 | Allgeier et al. |
| 2013/0172579 | A1 | 7/2013 | Desilva et al. |
| 2013/0172580 | A1 | 7/2013 | Ritter et al. |
| 2013/0172586 | A1 | 7/2013 | Desilva et al. |
| 2013/0172629 | A1 | 7/2013 | Allgeier et al. |
| 2013/0184495 | A1 | 7/2013 | Dias et al. |
| 2013/0231505 | A1 | 9/2013 | Allgeier et al. |
| 2013/0289311 | A1 | 10/2013 | Allgeier et al. |
| 2013/0289312 | A1 | 10/2013 | Allgeier et al. |
| 2013/0289318 | A1 | 10/2013 | Allgeier et al. |
| 2013/0289319 | A1 | 10/2013 | Allgeier et al. |
| 2014/0081065 | A1 | 3/2014 | Sengupta et al. |
| 2014/0228596 | A1 | 8/2014 | Allgeier et al. |

FOREIGN PATENT DOCUMENTS

| | | |
|---|---|---|
| CN | 102190639 A | 9/2011 |
| DE | 4238493 C1 | 4/1994 |
| EP | 110089 B1 | 1/1988 |
| EP | 0411403 A1 | 2/1991 |
| EP | 0418925 A2 | 3/1991 |
| EP | 1243573 A1 | 9/2002 |
| EP | 1243673 A1 | 9/2002 |
| EP | 2390247 A1 | 11/2011 |
| JP | 2003183200 A | 7/2003 |
| JP | 2006036653 A | 2/2006 |
| KR | 100645668 B1 | 11/2006 |
| KR | 100688765 B1 | 2/2007 |
| WO | 9955654 A1 | 11/1999 |
| WO | 2007103586 A2 | 9/2007 |
| WO | 2007103586 A3 | 9/2007 |
| WO | 2009126852 A1 | 10/2009 |
| WO | 2009133787 A1 | 11/2009 |
| WO | 2010033789 A3 | 3/2010 |
| WO | WO2010033789 A2 | 3/2010 |
| WO | WO2010062689 A2 | 6/2010 |
| WO | 2010099201 A1 | 9/2010 |
| WO | 2010115759 A2 | 10/2010 |
| WO | WO2010115759 A2 | 10/2010 |
| WO | WO2010115759 A3 | 10/2010 |
| WO | 2010144873 A1 | 12/2010 |
| WO | WO2011149339 A1 | 3/2011 |
| WO | 2013027766 A1 | 2/2013 |
| WO | 2013066776 A1 | 5/2013 |
| WO | 2013109477 A1 | 7/2013 |

OTHER PUBLICATIONS

Shafizadeh et al Carbohydrate Res 71 1979 169-191.
Zanardi et al TetrahedronLetters 50 2009 999-1002.pdf.
Abe, R. et al, "Photocatalytic overall water splitting under visible light by TaON and WO3 with an IO3-/I-shuttle redox mediator", Chem Commun, 2005, 3829-3831.
Adkins, H. et al, "The catalytic hydrogenation of organic compounds over copper chromite", J Am Chem Soc (1931), vol. 53, 1093.
Alexeev, O.S. et al, "gamma-Al2O3-Supported Pt catalysts with extremely high dispersions resulting from Pt-W interactions", J Catal, 190 (2000) 157-17.
Binder et al., "Simple chemical transformation of lignocellulosic biomass into furans for fuels and chemicals", J Am Chem Soc (2009) 131, 1979-1985.
Buntara, T. et al, "Caprolactam from Renewable Resources: Catalytic Conversion of 5-Hydroxymethylfurfural into Caprolactone", Angew. Chem. Int. Ed. (2011), 50(31), 7083-7087.
Buntara, T. et al., "From 5-hydroxymethylfurfural (HMF) to polymer precursors: catalyst screening studies on the conversion of 1,2,6-hexanetriol to 1,6-hexanediol", Top Catal (2012) 55, 612-619.
Caes et al., "Conversion of Fructose into 5-(Hydroxymethyl)furfural in Sulfolane", ChemSusChem, (2011), 4(3), 353-356.
Chen, K. et al, "Chemoselective hydrogenolysis of tetrahydropyran-2-methanol to 1,6-hexanediol over rhenium-modified carbon-supported rhodium catalysts", ChemCatChem (2010) 2, 547-555.
Chen, K. et al, "C-O bond hydrogenolysis of cyclic ethers with OH groups over rhenium-modified supported iridium catalysts", J Catalysis (2012) vol. 294, 171-183.
Chia, M. et al, "Selective hydrogenolysis of polyols and cyclic ethers over bifunctional surface sites on rhodium-rhenium catalysts", J Am Chem Soc (2011) vol. 133, No. 32, 12675-12680.
Connor, R. et al, "Hydrogenolysis of Oxygenated Organic Compounds", J Am Chem Soc (1932), vol. 54, 4678-4690.
Diebold, U. "The surface science of titanium dioxide", Surface Science Reports 48 (2003) 53-229.
Efremov, A.A. et al, "Conversions of Levoglucosenone in Acid Media", Sibirskii Khimicheskii Zhurnal 1992, 6, 34-39 Translation.
Efremov, A.A., "Transformations of levoglucosenone at the anhydroglucoside bond", Chem Natural Compounds (1998) 34, 5, 582-589.
Efremov, A.A. et al, "New thermocatalytic methods of chemicals producing from lignocellulosic materials in the presence of acid-type catalysts", Intl Symposium Wood Pulping Chemistry, 8th, Helsinki (1995) 689-696.
French, G.J. et al, "A re-investigation of the thermal decomposition of ammonium paratungstate", J. Mat. Sci, 16 (1981) 3427-3436.
Gong, L. et al, "Selective hydrogenolysis of glycerol to 1,3-propanediol over a Pt/WO3/TiO2/SiO2 catalyst in aqueous media", Appl Catal A General 390 (2010) 119-126.
Gong, X.Q. et al, "Small Au and Pt Clusters at the Anatase TiO2(101) Surface: Behavior at Terraces, Steps, and Surface Oxygen Vacancies", J. Am. Chem. Soc. 130 (2008) 370-381.
Helberger et al, Justus Liebigs Annalen der Chemie (1949) 561, 215-220.
Huang, L. et al, "Direct conversion of glycerol into 1,3-propanediol over Cu-H4SiW12O40/SiO2 in vapor phase", Catal Lett, 131 (2009) 312-320.
Jalil, P.A. et al, "A Study of Stability of Tungstophosphoric Acid, H3PW12O40, Using Synchrotron XPS, XANES, Hexane Cracking, XRD and IR Spectroscopy", J. Catalysis, 2003, 217(2), 292-297.
Jayaraman, S. et al, "Synthesis and Characterization of Pt-WO3 as Methanol Oxidation Catalysts for Fuel Cells", J Phys Chem B, 2005, 109, 22958-22966.
Kamalakar, G. et al, "tert-Butylation of Phenol over Ordered Solid Acid Catalysts in Supercritical Carbon Dioxide: Efficient Synthesis of 2,4-Di-tert-butylphenol and 2,4,6-Tri-tert-butylphenol", Ind Eng Chem Res, 45 (2006) 6118-6126.
Karinen, R. et al, "Biorefining: heterogeneously catalyzed reactions of carbohydrates for the production of furfural and hydroxymethyfurfural", Chem Sus Chem (2011) 4, 1002-1016.
Kaufmann, W.E. et al, "The use of platinum oxide as a catalyst in the reduction of organic compounds. IV. Reduction of furfural and its derivatives", J Am Chem Soc (1923) 45, 3029-3044.

(56) References Cited

OTHER PUBLICATIONS

Kiss, A.B. et al, "Thermal polycondensation of ammonium paratungstate, (NH4)10[W12O40(OH)2].4H2O", J. Materials Sci, 13 (1978) 2541-2547.
Koso, S. et al, "Chemoselective hydrogenolysis of tetrahydrofurfuryl alcohol to 1,5-pentanediol", Chem. Commun. (2009) 2035-2037.
Koso, S. et al, "Promoting effect of Mo on the hydrogenolysis of tetrahydrofurfuryl alcohol to 1,5-pentanediol over Rh/SiO2", J Catalysis 267 (2009), 89-92.
Kuba, S. et al, "Structure and properties of tungstated zirconia catalysts for alkane conversion", J Catalysis, 216 (2003) 353-361.
Lee, U. et al, "Structure of pentasodium trihydrogenhexatungstoplatinate(IV) icosahydrate", Acta Cryst. (1983) C39, 817-819.
Liu, L. et al, "Mesoporous WO3 supported Pt catalyst for hydrogenolysis of glycerol to 1,3-propanediol", Chin. J Catal., 2012, 33, 1257-1261.
Nakagawa, Y. et al, "Heterogeneous catalysis of the glycerol hydrogenolysis", Catal Sci Technol 2011, 1, 179-190.
Nakagawa, Y. et al., "Production of 1,5-pentanediol from biomass via furfural and tetrahydrofurfuryl alcohol", Catalysis Today 195 (2012) 136-143.
Nikolla, E. et al., "'One-Pot' Synthesis of 5-(Hydroxymethyl)furfural from Carbohydrates Using Tin-Beta Zeolite", ACS Catal. (2011), 1, 408-410.
Okuhara, T. et al, "Insoluble heteropoly compounds as highly active catalysts for liquid-phase reactions", J. Mol. Catal. 74 (1992) 247-256.
Ott, L. et al, "Catalytic Dehydration of Glycerol in sub- and supercritical water: a new chemical process for acrolein production", Green Chemistry, 2006, pp. 214-220, vol. 8.
Pae, Y.I. et al, "Characterization of NiO-TiO2 modified with WO3 and catalytic activity for acid catalysis", Bull. Korean Chem. Soc. 2004, vol. 25(12), 1881-1888.
Roman-Leshkov, Y. et al., "Solvent effects on fructose dehydration to 5-hydroxymethylfurfural in biphasic systems saturated with inorganic salts", Top Catal (2009) 52:297-303.
SRI Process Economics Program, 31, Hexamethylenediamine Nov. 1967.
Ten Dam, J. et al, "Pt/Al2O3 catalyzed 1,3-propanediol formation from glycerol using tungsten additives", ChemCatChem (2013), 5(2), 497-505.
Tong, X. et al, "Biomass into chemicals: conversion of sugars to furan derivatives by catalytic processes", Appl. Catalysis A General, 385 (2010) 1-13.
Tripathy, P.K. et al, "A comparative study on the thermal decomposition of ammonium p-tungstate in batch and fluidized-bed reactors", Ind Eng Chem Res 36 (1997) 3602-3606.
Trost, B. M. "Cyclizations Made Easy by Transition Metal Catalysts", in Homogeneous Transition Metal Catalyzed Reactions; Moser, W. et al; Adv. Chem. 31, 1992, ACS, Washington, DC.
Xu, W. et al, "Direct catalytic conversion of furfural to 1,5-pentanediol by hydrogenolysis of the furan ring under mild conditions over Pt/Co2AlO4 catalyst" Chem Comm, Royal Society of Chemistry (2011) vol. 47, No. 13, 3924-3926.
Yamazoe, S. et al, "XAFS Study of Tungsten L1-, L3- Edges: Structural Analysis of Loaded Tungsten Oxide Species", Envir Sci, Research Frontiers 2008, Spring 8, 138-139.
Yamazoe, S. et al, "XAFS Study of Tungsten L1- and L3-Edges: Structural Analysis of WO3 Species Loaded on TiO2 as a Catalyst for Photo-oxidation of NH3", J. Phys Chem C 2008, 112, 6869-6879 .
Yoshinaga, Y. et al, "Shape-selective oxidation catalysed by a Pt-promoted ultramicroporous heteropoly compound", J.Chem. Soc. Faraday Trans 1998, 94(15) 2235-2240.
Database CAPLUS on STN, AN 1979:151575, Nishino et al, JP 53149905 A, Dec. 27, 1978 (abstract).
Database WPIX on STN, AN 1979-11181B [197906], Nishino et al, JP53149905 A Dec. 27, 1978 (abstract).
Office action dated Apr. 9, 2014 for copending U.S. Appl. No. 13/870,080.
Alamillo, R. et al., "Selective Hydrogenation of Biomass-Derived 5-Hydroxymethylfurfural Using Heterogeneous Catalysts", Green Chem., 2012, 14, 1413.
Jung, K.J. et al., "Furfural Decarbonylation Catalyzed by Charcoal Supported Palladium: Part I—Kinetics", Biomass 16 (1988) 63-76.
Jung, K.J. et al., "Furfural Decarbonylation Catalyzed by Charcoal Supported Palladium: Part II—A Continuous Process", Biomass 16 (1988) 89-96.
Lichtenthaler, F.W. "Carbohydrates as Organic Raw Materials" 2010 Wiley-VCH Verlag GmbH&Co. KGaA, Weinheim 10.1002/14356007.n05_n07.
Qin, L.-Z. et al., "Aqueous-phase deoxygenation of glycerol to 1,3-propanediol over Pt/WO3/ZrO2 catalysts in a fixed-bed reactor", Green Chem., 2010, 12, 1466-1472.
Rao, R.S. et al., "Furfural Hydrogenation Over Carbon-Supported Copper", Catalysis Letters 60 (1999) 51-57.
Zheng, H.-Y. et al., "Towards Understanding the Reaction Pathway in Vapour Phase Hydrogenation of Furfural to 2-Methylfuran", J Molecular Catalysis A: Chemical 246 (2006) 18-23.
International Search Report dated May 6, 2014, PCT/US2012/062314.
Copending application No. PCT/US14/23874 filed Mar. 12, 2014.
Copending application No. PCT/US14/23905 filed Mar. 12, 2014.
Notice of allowance dated Apr. 28, 2014 for copending U.S. Appl. No. 13/729,494.
Office action dated May 7, 2014 for copending U.S. Appl. No. 13/729,390.
Notice of allowance dated Jun. 10, 2014 for copending U.S. Appl. No. 13/870,091.
Notice of allowance dated Jun. 23, 2014 for copending U.S. Appl. No. 13/870,072.
Notice of allowance dated Apr. 29, 2014 for copending U.S. Appl. No. 13/729,507.
International Search Report dated Mar. 29, 2013, PCT/US2012/062314.
International Search Report dated Apr. 29, 2013, PCT/US2012/071891.
International Search Report dated Apr. 29, 2013, PCT/US2012/071907.
International Search Report dated Apr. 29, 2013, PCT/US2012/071893.
International Search Report dated Apr. 29, 2013, PCT/US2012/071912.
International Search Report dated Apr. 30, 2013, PCT/US2012/071894.
International Search Report dated Jul. 26, 2013, PCT/US2013/038403.
International Search Report dated Jul. 18, 2013, PCT/US2013/038418.
International Search Report dated Jul. 24, 2013, PCT/US2013/038441.
International Search Report dated Jul. 24, 2013, PCT/US2013/038436.
International Preliminary Report on Patentability, PCT International Application PCT/US2012/062314 dated May 15, 2014.
International Preliminary Report on Patentability, PCT International Application PCT/US2012/071891 dated Jul. 10, 2014.
International Preliminary Report on Patentability, PCT International Application PCT/US2012/071907 dated Jul. 10, 2014.
International Preliminary Report on Patentability, PCT International Application PCT/US2012/071893 dated Jul. 10, 2014.
International Preliminary Report on Patentability, PCT International Application PCT/US2012/071912 dated Jul. 10, 2014.
International Preliminary Report on Patentability, PCT International Application PCT/US2012/071894 dated Jul. 10, 2014.
Office action dated Dec. 20, 2013 for co-pending U.S. Appl. No. 13/729,507.
Office actions dated Jun. 26, 2013, Sep. 13, 2013, and May 7, 2014 for co-pending U.S. Appl. No. 13/729,390.
Co-Pending International Patent Application, PCT/US2014/023874 Filed Mar. 12, 2014.
Co-Pending International Patent Application, PCT/US2014/023095 Filed Mar. 12, 2014.

PROCESS FOR PREPARING 1, 6-HEXANEDIOL

This application claims priority under 35 U.S.C. §119(e) from, and claims the benefit of, U.S. Provisional Application No. 61/582,067, filed Dec. 30, 2011; U.S. Provisional Application No. 61/639,404 filed Apr. 27, 2012; U.S. Provisional Application No. 61/639,436 filed Apr. 27, 2012; and U.S. Provisional Application No. 61/639,449 filed Apr. 27, 2012; all of which are by this reference incorporated in their entirety as a part hereof for all purposes.

FIELD OF DISCLOSURE

The present invention relates to processes for preparing 1,6-hexanediol.

BACKGROUND

Industrial chemicals obtained from inexpensive sources are desirable for use in industrial processes, for example as raw materials, solvents, or starting materials. It has become increasingly desirable to obtain industrial chemicals or their precursors from materials that are not only inexpensive but also benign in the environment. Of particular interest are materials which can be obtained from renewable sources, that is, materials that are produced by a biological activity such as planting, farming, or harvesting. As used herein, the terms "renewable" and "biosourced" can be used interchangeably.

Biomass sources for such materials are becoming more attractive economically versus petroleum-based ones. Although the convergent and selective synthesis of $C_5$ and $C_6$ carbocyclic intermediates from biomass is difficult because of the high degree of oxygenation of many components of biomass, use of such biomass-derived intermediates as feedstocks would offer new routes to industrially useful chemicals.

1,6-Hexanediol is a useful intermediate in the industrial preparation of nylon. For example, 1,6-hexandiol can be converted by known methods to 1,6-hexamethylene diamine, a useful monomer in nylon production.

There is an existing need for processes to produce 1,6-hexanediol, and synthetic intermediates useful in the production of 1,6-hexanediol, from renewable biosources. There is an existing need for processes to produce 1,6-hexanediol, as well as synthetic intermediates useful in the production of 1,6-hexanediol, from biomass-derived starting materials, including $C_6$ oxygenated hydrocarbons such as levoglucosenone.

SUMMARY

In one embodiment, a process is disclosed, the process comprising the steps of
a) contacting levoglucosenone with hydrogen in the presence of a first hydrogenation catalyst at a first temperature between about 25° C. and about 150° C. to form product mixture (I); and
b) heating product mixture (I) in the presence of hydrogen and a second hydrogenation catalyst at a second temperature between about 120° C. and about 260° C. to form product mixture (II).

In one embodiment, product mixture (I) comprises one or more of levoglucosenol, levoglucosanol, tetrahydrofuran 2,5-dimethanol, 2-hydroxymethyltetrahydropyran, 1,2,5,6-tetrahydroxyhexane, 1,2,6-hexanetriol, and 2-hydroxymethyl-5-hydroxytetrahydropyran.

In one embodiment, product mixture (II) comprises one or more of 1,2,6-hexanetriol, tetrahydrofuran 2,5-dimethanol, 2-hydroxymethyl-5-hydroxytetrahydropyran, 1,6-hexanediol, 1,2-hexanediol, 1-hexanol, and 2-hydroxymethyltetrahydropyran.

DETAILED DESCRIPTION

As used herein, where the indefinite article "a" or "an" is used with respect to a statement or description of the presence of a step in a process disclosed herein, unless the statement or description explicitly provides to the contrary, the use of such indefinite article does not limit the presence of the step in the process to one in number.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. The term "about" may mean within 10% of the reported numerical value, preferably within 5% of the reported numerical value.

As used herein, the term "biomass" refers to any hemicellulosic or lignocellulosic material and includes materials comprising hemicellulose, and optionally further comprising cellulose, lignin, starch, oligosaccharides and/or monosaccharides.

As used herein, the term "lignocellulosic" means comprising both lignin and cellulose. Lignocellulosic material may also comprise hemicellulose. In some embodiments, lignocellulosic material contains glucan and xylan.

Hemicellulose is a non-cellulosic polysaccharide found in lignocellulosic biomass. Hemicellulose is a branched heteropolymer consisting of different sugar monomers. It typically comprises from 500 to 3000 sugar monomeric units.

Lignin is a complex high molecular weight polymer and can comprise guaiacyl units as in softwood lignin, or a mixture of guaiacyl and syringyl units as in hardwood lignin.

As used herein, the abbreviations "Lgone" and "LGone" refer to levoglucosenone, also known as 1,6-anhydro-3,4-dideoxy-p-D-pyranosen-2-one. The chemical structure of levoglucosenone is represented by Formula (I).

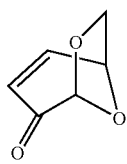

I

As used herein, the abbreviations "Lgol" and "LGol" refer to levoglucosanol, also known as 1,6-anhydro-3,4-dideoxy-hexopyranose, and include a mixture of the threo and erythro stereoisomers. The chemical structure of 1,6-anhydro-3,4-dideoxyhexopyranose is represented by Formula (II).

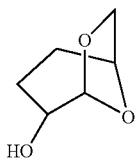

II

As used herein, the abbreviation "K128" refers to 1,6-anhydro-3,4-dideoxy-p-D-pyranose-2-one. The chemical structure of 1,6-anhydro-3,4-dideoxy-p-D-pyranose-2-one is represented by Formula (III).

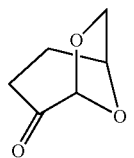

III

As used herein, the abbreviation "Tetraol" refers to 1,2,5,6-tetrahydroxyhexane, also known as 3,4-dideoxyhexitol, and includes a mixture of stereoisomers. The chemical structure of 1,2,5,6-tetrahydroxyhexane is represented by Formula (IV).

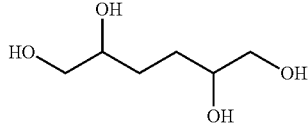

IV

As used herein, the abbreviation "THFDM" refers to tetrahydro-2,5-furandimethanol, also known as 2,5-bis[hydroxymethyl]tetrahydrofuran, and includes a mixture of stereoisomers (cis- and racemic trans-isomers). The chemical structure of tetrahydro-2,5-furandimethanol is represented by Formula (V).

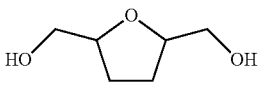

V

As used herein, the abbreviation "1,2,6-HT" refers to 1,2,6-hexanetriol and includes a racemic mixture of isomers. The chemical structure of 1,2,6-hexanetriol is represented by Formula (VI).

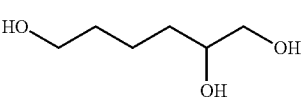

VI

As used herein, the abbreviation "THPM" refers to tetrahydro-2H-pyran-2-methanol, also known as 2-hydroxymethyltetrahydropyran, and includes a racemic mixture of isomers. The chemical structure of tetrahydro-2H-pyran-2-methanol is represented by Formula (VII).

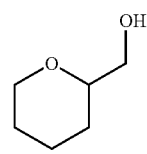

VII

As used herein, the abbreviation "HOTHPM" refers to 2-hydroxymethyl-5-hydroxytetrahydro-2H-pyran, also known as 1,5-anhydro-3,4-dideoxyhexitol, and includes a mixture of stereoisomers. The chemical structure of 2-hydroxymethyl-5-hydroxytetrahydro-2H-pyran is represented by Formula (VIII).

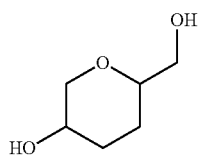

VIII

As used herein, the abbreviation "1,6-HD" refers to 1,6-hexanediol. The chemical structure of 1,6-hexanediol is represented by Formula (IX).

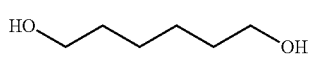

IX

As used herein, the abbreviation "1,2-HD" refers to 1,2-hexanediol and includes a racemic mixture of isomers. The chemical structure of 1,2-hexanediol is represented by Formula (X).

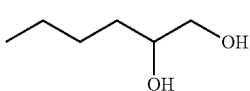

X

As used herein, the abbreviation "1,2-CHD" refers to 1,2-cyclohexanediol and includes a mixture of stereoisomers (cis and racemic trans isomers). The chemical structure of 1,2-cyclohexanediol is represented by Formula (XI).

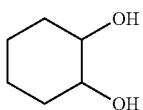

XI

As used herein, the abbreviation "1,5-HD" refers to 1,5-hexanediol and includes a racemic mixture of isomers. The chemical structure of 1,5-hexanediol is represented by Formula (XII).

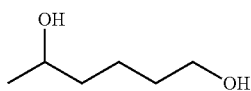

XII

As used herein, the abbreviation "HexOH" refers to 1-hexanol. The chemical structure 1-hexanol is represented by Formula (XIII).

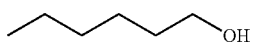

XIII

As used herein, the abbreviation "PentOH" refers to 1-pentanol. The chemical structure 1-pentanol is represented by Formula (XIV).

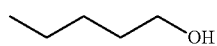

XIV

As used herein, the abbreviation "A128" refers to 1,6-anhydro-3,4-dideoxy-β-erythro-hex-3-enopyranose, also known as levoglucosenol. The chemical structure of A128 is represented by Formula (XV).

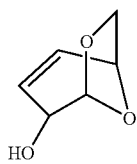

XV

As used herein, the abbreviation "1,5-PD" refers to 1,5-pentanediol The chemical structure of 1,5-PD is represented by Formula (XVI).

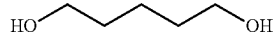

XVI

Disclosed herein are processes for obtaining 1,6-hexanediol, and synthetic intermediates useful in the production of 1,6-hexanediol, from levoglucosenone, which in turn can be derived from a renewable biosource. As used herein, the term "renewable biosource" includes biomass and animal or vegetable fats or oils.

A renewable biosource can be pyrolyzed under high temperature conditions in the presence of an acid catalyst to provide useful chemical intermediates. For example, pyrolysis of wood, starch, glucose or cellulose can produce levoglucosenone by known and conventional methods (see, for example, Ponder (*Applied Biochemistry and Biotechnology*, Vol 24/25, 41-41 (1990)) or Shafizadeh (*Carbohydrate Research*, 71, 169-191 (1979)). In some embodiments, levoglucosenone as obtained by pyrolysis of biomass contains small amounts of acidic components, for example levulinic acid.

In the processes disclosed herein, levoglucosenone is contacted with hydrogen in the presence of a first hydrogenation catalyst at a first temperature between about 25° C. and about 150° C. to form product mixture (I), which is then heated in the presence of hydrogen and a second hydrogenation catalyst at a second temperature between about 120° C. and about 260° C. to form product mixture (II). Product mixture (I) comprises one or more of 1,6-anhydro-3,4-dideoxy-ρ-D-pyranose-2-one, levoglucosenol, levoglucosanol, tetrahydrofuran-2,5-dimethanol, 2-hydroxymethyltetrahydropyran, 1,2,5,6-tetrahydroxyhexane, 1,2,6-hexanetriol, and 2-hydroxymethyl-5-hydroxytetrahydropyran, each of which can be a useful chemical intermediate in the synthesis of 1,6-hexanediol. Product mixture (II) comprises one or more of 1,2,6-hexanetriol, tetrahydrofuran-2,5-dimethanol, 2-hydroxymethyl-5-hydroxytetrahydropyran, 1,6-hexanediol, 1,2-hexanediol, 1-hexanol, and 2-hydroxymethyltetrahydropyran.

In the processes disclosed herein, levoglucosanol may be produced and converted as a mixture of stereoisomers (threo- and erythro isomer); tetrahydrofuran-2,5-dimethanol may be produced and converted as a mixture of stereoisomers (cis- and trans isomer with respect to the hydroxymethy groups attached to the tetrahydrofuran ring: one cis meso compound a trans racemate); 2-hydroxymethyltetrahydropyran may be produced and converted as a racemate; 1,2,5,6-tetrahydroxyhexane may be produced and converted as a mixture of stereoisomers differing only in the configuration of the C2 and C5 carbon atom (one meso compound and a racemate); 1,2,6-hexanetriol may be produced and converted as racemate; 2-hydroxymethyl-5-hydroxytetrahydropyran may be produced and converted as a mixture of stereoisomers (two racemic stereoisomers); and 1,2-hexanediol may be produced and converted as a racemate.

For contacting with hydrogen in the presence of a first hydrogenation catalyst, the levoglucosenone is typically dissolved or suspended in a liquid medium, referred to herein as a "solvent". Suitable solvents include water, a $C_1$-$C_{20}$ alcohol, a $C_2$-$C_{20}$ ether, a $C_2$-$C_{20}$ ester, or mixtures thereof. Examples of suitable alcohols which are commercially available include methanol, ethanol, propanol, butanol, and hexanol. Examples of suitable ethers which are commercially available include dibutylether, dihexylether, methyl-t-butyl-ether, tetrahydrofuran, and dioxane. Examples of suitable esters which are commercially available include ethyl acetate, butyl acetate, methyl butyrate, ethyl butyrate, butyl butyrate and hexyl acetate.

The concentration of levoglucosenone in the solvent, whether dissolved or as a suspension, is between about 1 wt % and about 50 wt %; in some embodiments it is between and optionally includes any two of the following values: 1 wt %, 5 wt %, 10 wt %, 15 wt %, 20 wt %, 25 wt %, 30 wt %, 35 wt %, 40 wt %, 45 wt %, and 50 wt %. It is anticipated that higher concentrations of levoglucosenone in water, or even neat levoglucosenone, could be used. The optimal concentration will depend on the intended reaction conditions.

The first hydrogenation catalyst can be homogeneous or heterogenous. The first hydrogenation catalyst comprises one or more of supported platinum catalysts, supported palladium catalysts, supported ruthenium catalysts, supported nickel catalysts, catalysts derived from nickel-aluminum alloys, catalysts derived from cobalt-aluminum alloys, and organophosphorous or organometallic complexes of Rh, Ir, Ru, or Ti. Examples of commercially available catalysts suitable for use as the first hydrogenation catalyst include RANEY® nickel, RANEY® cobalt, palladium on carbon, palladium on alumina, platinum on carbon, ruthenium on carbon, and organophosphorous or organometallic complexes of Rh, Ir, Ru, or Ti, for example chlorotris(triphenylphosphine)rhodium(I) [CAS#14694-95-2], (tricyclohexylphosphine)(1,5-cyclooctadiene)(pyridine)iridium(I)hexafluorophosphate [CAS#64536-78-3], bis(pentamethylcyclopentadienyl)titanium(IV) dichloride [CAS#11136-36-0], chloro[rac-2,2'-bis(diphenylphosphino)-1,1'-binaphthyl](p-cymene) ruthenium (II) chloride [RuCl(p-cymene)(binap)]Cl [CAS#145926-28-9], and a combination of bis(diphenylphosphino)ethane [CAS#1663-45-2] and bis(1,5-cyclooctadiene)rhodium(I) tetrafluoroborate [CAS#35138-22-8]

Hydrogen, optionally in combination with an inert gas such as nitrogen or argon, is contacted with the levoglucosenone and the first hydrogenation catalyst at a total applied pressure which can range from ambient pressure (i.e., 0 applied pressure) to about 1000 psi. In some embodiments, the applied pressure is between and optionally includes any two of the following values: 0, 50, 100, 200, 300, 400, 500, 600, 700, 800, 900, and 1000 psi. If an inert gas is used in combination with the hydrogen, the amount of the inert gas should be such that it does not negatively impact the formation of product mixture (I).

The levoglucosenone, first hydrogenation catalyst, and hydrogen are contacted at a first temperature between about 25° C. and about 150° C., for example between about 50° C. and about 100° C. In some embodiments, the temperature is between and optionally includes any two of the following values: 25° C., 30° C., 40° C., 50° C., 60° C., 70° C., 80° C., 90° C., 100° C., 110° C., 120° C., 130° C., 140° C., and 150° C. The contacting is performed for a period of time sufficient to react at least about 90%, for example at least about 95%, of the sum of levoglucosenone and any 1,6-anhydro-3,4-dideoxy-p-D-pyranose-2-one isomers and/or 1,6-anhydro-3,4-dideoxy-β-erythro-hex-3-enopyranose isomers to one or more chemical species, including levoglucosanol.

At the end of the designated contacting time, if desired, the first hydrogenation catalyst can be separated from product mixture (I) by methods known in the art, for example by filtration. After separation from the catalyst, if desired the product mixture components, including one or more of levoglucosanol, tetrahydrofuran-2,5-dimethanol, 2-hydroxymethyltetrahydropyran, 1,2,5,6-tetrahydroxyhexane, 1,2,6-hexanetriol, and 2-hydroxymethyl-5-hydroxytetrahydropyran, can be separated from one another using any appropriate method known in the art, for example distillation. In one embodiment, product mixture (I) comprises levoglucosenol. In one embodiment, product mixture (I) comprises tetrahydrofuran-2,5-dimethanol. In one embodiment, product mixture (I) comprises 2-hydroxymethyltetrahydropyran. In one embodiment, product mixture (I) comprises 1,2,5,6-tetrahydroxyhexane. In one embodiment, product mixture (I) comprises 1,2,6-hexanetriol. In one embodiment, product mixture (I) comprises 2-hydroxymethyl-5-hydroxytetrahydropyran.

Product mixture (I) is then heated in the presence of hydrogen and a second hydrogenation catalyst at a temperature between about 120° C. and about 260° C. to form product mixture (II). In one embodiment, product mixture (I) is dissolved or suspended in a solvent, which can be the same or different from any solvent used with the levoglucosenone in the first step of the process. In one embodiment, product mixture (I) is used without any added solvent.

In some embodiments, the second hydrogenation catalyst comprises a metal M1 and a metal M2 or an oxide of M2, and optionally a solid support, wherein:

M1 is Pd, Pt, or Ir; and M2 is Mo, W, V, Mn, Re, Zr, Ni, Cu, Zn, Cr, Ge, Sn, Ti, Au, or Co; or M1 is Rh and M2 is Re, Mo, W, V, Mn, Ni, Cu, Zn, Cr, Ge, Sn, Ti, Au, or Zr; or M1 is Ag, Au or Co; and M2 is Re, Mo, or W;

M1 is Cu, Pd, Fe, or Ni; and M2 is Re, Mo, Cu, Zn, Cr, Ge, Sn, or W; or

M1 is Ag, Pt, Cu, or Au, and M2 is Ni, Fe, Sn, Ge, or Ir; or

M1 is Co and M2 is Fe; or

M1 is Ni and M2 is Co or Fe; or

M1 is Mn and M2 is Cr.

The M1 and M2 components of the catalysts may be derived from any appropriate metal compound. Examples include but are not limited to: rhodium (III) chloride hydrate, copper (II) nitrate hydrate, nickel (II) chloride hexahydrate, iridium (IV) chloride hydrate, iron (III) nitrate nonahydrate, tetraammineplatinum (II) nitrate, platinum chloride, hexachloroplatinic acid, tetrachloroplatinic acid, palladium chloride, palladium nitrate, palladium acetate, iridium trichloride, ammonium perrhenate, ammonium tungsten oxide hydrate, ammonium molybdate hydrate, manganese (II) nitrate hydrate, and ammonium vanadium oxide.

The loading of M1 may be 0.1-50% but preferably 0.5-5% by weight, based on the weight of the prepared catalyst (i.e., including the solid catalyst support where present). The loading of M2 may be 0.1-99.9%, preferably 2-10%. Preferably the atomic ratio of M1 to M2 in catalysts containing both M1 and M2 is 1:0.5 to 1:5. Optionally, M2 may be incorporated into the catalyst support or serve as the catalyst support, e.g. Pt supported on tungsten oxide or molybdenum oxide. Regarding the catalyst, all percentages are interpreted as weight percent relative to the weight of the prepared catalyst.

In some embodiments, the second hydrogenation catalyst comprises metals M1, M2, and M3 and optionally a support, wherein M1 is Mn, Cr, V, or Ti; M2 is Ni, Co, or Fe; and M3 is Cu, Ag, Pt, Pd or Au; or M1 is Pt or Rh; M2 is Cu, Ni or Pd; and M3 is Mo, Re or W.

In some embodiments, the second hydrogenation catalyst comprises a Cu component; optionally a heteropoly acid component; optionally a second metal or metal oxide; optionally one or more promoters; and optionally a support, wherein:

the Cu component comprises Cu or a Cu oxide;

the heteropoly acid component is $H_3[P(W_3O_{10})_4]$, $H_4[Si(W_3O_{10})_4]$, $Cs_{2.5}H_{0.5}[P(W_3O_{10})_4]$; phosphomolybdic acid, or silicomolybdic acid;

the second metal or metal oxide is Cr, a Cr oxide, Ni, a Ni oxide, Mn, a Mn oxide, Zn, or a Zn oxide; and the one or more promoters are selected from the group consisting of Ba, Ce, Mg, Na, K.

In some embodiments, the catalyst comprises CuO. In some embodiments, the catalyst comprises from 2 wt % to 98 wt % CuO and further comprises from 98 wt % to 2 wt % of at least one oxide selected from the group consisting of zinc oxide (ZnO), magnesium oxide (MgO), barium oxide (BaO), chromium oxide ($Cr_2C_3$), silica ($SiO_2$), alumina ($Al_2C_3$), nickel oxide (NiO), manganese oxide ($MnO_2$), sodium oxide ($Na_2O$), potassium oxide ($K_2O$), cerium oxide ($CeO_2$), lanthanum oxide ($La_2C_3$), iron oxide ($Fe_2C_3$), silver oxide ($Ag_2O$) and cobalt oxide ($Co_2C_3$), based on the total weight of the catalyst. In one embodiment, the catalyst further comprises ZnO. In one embodiment, the catalyst further comprises MgO. In some embodiments, the catalyst further comprises carbon. Examples of suitable commercially available catalysts include but are not limited to the following: CuO/ZnO, BaO/CuO/$Cr_2C_3$/$SiO_2$, BaO/CuO/$Cr_2C_3$, BaO/CuO/$MnO_2$/$Cr_2C_3$, CuO/$SiO_2$, CuO/$Al_2C_3$, CuO/NiO/$Al_2C_3$, CuO/$Cr_2C_3$/$MnO_2$, CuO/$Cr_2C_3$, CuO/$MnO_2$/$Al_2C_3$, CuO/$Cr_2C_3$, CuO/ZnO/$Al_2C_3$, CuO/$SiO_2$/$Cr_2C_3$/MgO, CuO/ZnO/$CeO_2$/$Al_2C_3$/$Na_2O$/C, CuO/NiO, and NiO/CuO/$K_2O$/$Cr_2C_3$/$CaF_2$. In one embodiment, the catalyst comprises CuO/ZnO, CuO/ZnO/$Al_2C_3$, or CuO/ZnO/$CeO_2$/$Al_2C_3$/$Na_2O$/C.

Hydrogenation catalysts suitable for use in the second step of the processes disclosed herein can be synthesized by, for example, mixing the Cu component with a solution of the heteropolyacid component, evaporating the solvent (e.g., water) to dryness and calcining the resulting powder. The heteropolyacid component may itself be provided as a solution of heteropolyacid and a basic salt, for example, a solution containing a mixture of $H_3[P(W_3C_{10})_4]$ and cesium carbonate in suitable proportions to form $Cs_{2.5}H_{0.5}[P(W_3O_{10})_4$ In some embodiments, it is useful to utilize a solid catalyst support to enhance the stability and economic feasibility of the process. Examples of supports include, without limitation: $WO_3$, $SiO_2$, $Al_2C_3$, carbon, $TiO_2$, $ZrO_2$, $CeO_2$, $SiO_2$—$Al_2C_3$, clays (e.g., montmorillonite), $SiO_2$—$TiO_2$, tungstated $ZrO_2$, zeolites (such as H—Y zeolite), $V_2C_5$, and $MoO_3$. In other embodiments, it may be desirable to not have a solid support.

The prepared hydrogenation catalyst can be in any physical form typical for heterogeneous catalysts, including but not limited to: powdered (also known as "fluidized") forms with 0.01-150 μm particle size, formed tablets, extrudates, spheres, engineered particles having uniform 0.5-10 mm size, monolithic structures on which surfaces the catalyst is applied, or combinations of two or more of the above. When a solid support is utilized a catalyst containing both M1 and M2, it is desirable that M1 be intimately associated with the M2 component, the M3 component, or both, as measured by transmission electron microscopy with energy dispersive spectroscopy. It is further preferable that the particle size of the M1 component be less than 10 nm and most preferably less than 3 nm as measured by the same techniques. In this case, particle size of the M1 component may be interpreted as particle size of a mixture of the M1 and M2 components, an alloy of the M1 and M2 components, a particle of the M1 component adjacent to a particle of the M2 component, or a particle of the M1 component on the support which contains the M2 component.

The second hydrogenation catalysts can be synthesized by any conventional method for preparing catalysts, for example, deposition of metal salts from aqueous or organic solvent solutions via impregnation or incipient wetness, precipitation of an M1 component and/or an M2 component and/or an M3 component, or solid state synthesis. Preparation may comprise drying catalyst materials under elevated temperatures from 30-250° C., preferably 50-150° C.; calcination by heating in the presence of air at temperatures from 250-800° C., preferably 300-450° C.; and reduction in the presence of hydrogen at 100-400° C., preferably 200-300° C., or reduction with alternative reducing agents such as hydrazine, formic acid or ammonium formate. The above techniques may be utilized with powdered or formed particulate catalyst materials prepared by tableting, extrusion or other techniques common for catalyst synthesis. Where powdered catalysts materials are utilized, it will be appreciated that the catalyst support or the resulting catalyst material may be sieved to a desired particle size and that the particle size may be optimized to enhance catalyst performance.

Hydrogen, optionally in combination with an inert gas such as nitrogen or argon, is present during the heating of product mixture (I) in the presence of the second hydrogenation catalyst. The total applied pressure can range from 100 psi to about 2000 psi. In some embodiments, the applied pressure is between and optionally includes any two of the following values: 100, 200, 300, 400, 500, 600, 700, 800, 900, and 2000 psi. If an inert gas is used in combination with the hydrogen, the amount of the inert gas should be such that it does not negatively impact the formation of product mixture (II).

The second temperature is between about 120° C. and about 260° C., for example between about 140° C. and about 200° C. In some embodiments, the temperature is between and optionally includes any two of the following values: 120° C., 130° C., 140° C., 150° C., 160° C., 170° C., 180° C., 190° C., 200° C., 210° C., 220° C., 230° C., 240° C., 250° C., and 260° C.

At the end of the designated heating time, if desired, the second hydrogenation catalyst can be separated from product mixture (II) by methods known in the art, for example by filtration. After separation from the catalyst, if desired the product mixture components, including one or more of tetrahydrofuran-2,5-dimethanol, 2-hydroxymethyltetrahydropyran, 1,2,6-hexanetriol, 2-hydroxymethyl-5-hydroxytetrahydropyran, 1,2-hexanediol, 1-hexanol, and 1,6-hexanediol can be separated from one another using any appropriate method known in the art, for example distillation. In one embodiment, product mixture (II) comprises 1,6-hexanediol. In one embodiment, product mixture (II) comprises tetrahydrofuran-2,5-dimethanol. In one embodiment, product mixture (II) comprises 2-hydroxymethyltetrahydropyran. In one embodiment, product mixture (II) comprises 1,2,6-hexanetriol. In one embodiment, product mixture (II) comprises 2-hydroxymethyl-5-hydroxytetrahydropyran. In one embodiment, product mixture (II) comprises 1,2-hexanediol. In one embodiment, product mixture (II) comprises 1-hexanol.

The first and second steps of the processes can be run in batch or continuous modes, in liquid phase, gas phase, or biphasic conditions. In a batch or continuous mode of operation, the amount of each catalyst used will depend on the specific equipment configuration and reaction conditions.

EXAMPLES

The methods disclosed herein are illustrated in the following examples. From the above discussion and these examples, one skilled in the art can ascertain the essential characteristics of this invention, and without departing from the spirit and scope thereof, can make various changes and modifications of the invention to adapt it to various uses and conditions.

All commercial materials were used as received unless stated otherwise and were obtained from Sigma-Aldrich (St. Louis, Mo.) unless stated otherwise. Levoglucosenone (90% purity) was obtained from TimTec LLC (Newark, Del.). 2,5-Tetrahydrofurandimethanol was obtained from the PenAKem corporation (Memphis, Tenn.). 5% Platinum on carbon (Pt/C) and 5% palladium on carbon (Pd/C) were received from the Aldrich Chemical Company (Aldrich catalogue numbers 20,5931 and 33,012-4, respectively). 1,6-anhydro-3,4-dideoxy-p-D-pyranose-2-one ("K128") and 1,6-anhydro-3,4-dideoxy-β-erythro-hex-3-enopyranose ("A128") were prepared as described in Journal of Organic Chemistry, 63 (1998) 8133-8144.

Copper catalysts of various compositions were received from different commercial sources as described below. All copper catalysts were ground with a mortar and pestle and passed through a 0.0165" mesh sieve prior to use.

TABLE 1

Copper Catalysts Used in Some of the Examples

| Catalyst Name | Vendor | Vendor Catalog Number | Composition |
|---|---|---|---|
| $BaO/CuO/Cr_2O_3$ | SuedChemie | G-22 | $CuO$ 41%, $Cr_2O_3$ 43%, $BaO$ 12% |
| $BaO/CuO/MnO_2/Cr_2O_3$ | SuedChemie | G-99B-0 | $CuO$ 47%, $Cr_2O_3$ 46%, $MnO_2$ 4%, $BaO$ 2% |
| $CuO/MnO_2/Al_2O_3$ | SuedChemie | T-4489 | $CuO$ 56%, $MnO_2$ 10%, $Al_2O_3$ 34% |
| $CuO/ZnO/Al_2O_3$ | SuedChemie | ActiSorb ® 301 | $CuO$ 53%, $ZnO$ 27%, $Al_2O_3$ 20% |
| $CuO/ZnO$ | SuedChemie | T-2130 | $CuO$ 33%, $ZnO$ 66% |
| $CuO/SiO_2$ (BASF Cu-0860) | BASF | Cu-0860 | Decan-1-ol 30.0-50.0%, Copper 25.0-40.0%, Silicon dioxide 10.0-20.0%, Calcium oxide 0.0-10.0%, Copper oxide 0.0-10.0%, Palygorskite 0.0-7.0%, Crystalline silica 0.0-1.0% |
| $CuO/ZnO/CeO_2/Al_2O_3/Na_2O/C$ | Johnson Matthey | PRICAT CZ 30/18 T 6*5 mm | $CuO$ 39 wt.%, $ZnO$ 45 wt. %, $Ce_2O_3$ 2 wt. %, $Al_2O_3$ 8 wt. %, $Na_2O$ 0.3 wt. %, Graphite 2.5 wt. %, $H_2O$, $CO_2$ Balance |

The $Pt/W/TiO_2$ catalyst was synthesized using the following procedure. 0.92 Grams of Aerolyst 7708 $TiO_2$ (Evonik) that had been ground with a mortar and pestle and passed through a 0.0165" mesh sieve, then wetted with 1.0 ml of deionized water, was impregnated with 0.08 g of tetraammineplatinum (II) nitrate (Strem, Cat #78-2010) dissolved in 1.0 ml of deionized water. The resulting wet suspension was vortexed for 15 minutes and then vacuum-dried at 110° C. overnight. The resulting precipitate was wetted with 1.0 ml of deionized water, and then 0.0535 g of ammonium tungsten oxide hydrate (para analogue) (Alfa, stock #22640) which had been thoroughly dissolved in 2.0 ml of deionized water was added on to the wetted precipitate. The resulting wet suspension was vortexed for 15 minutes and then vacuum-dried at 110° C. overnight. After reaching room temperature, the material was transferred to a ceramic boat and calcined in air at 400° C. for three hours. The calcined $Pt/W/TiO_2$ catalyst had a Pt loading of 4 wt % based on the total weight of the catalyst, and a 1:1 molar ratio of Pt:W.

Reactor feeds and reaction products were analyzed by gas chromatography using standard GC and GC/MS equipment: Agilent 5975C, HP5890, Stabilwax Column Restek Company Bellefonte, Pa. (30 m×025 mm 0.5 micron film thickness). Chemical components of reaction product mixtures were identified by matching their retention times and mass spectra to those of authentic samples.

The following abbreviations are used in the examples: "° C." means degrees Celsius; "wt %" means weight percent; "g" means gram; "min" means minute(s); "μL" means microliter; "wt %" means weight percent; "RV(s)" means reaction vessel(s); "PSI" means pounds per square inch; "mg/g" means milligram per gram; "μm" means micrometer; "mL" means milliliter; "mm" means millimeter and "mL/min" means milliliter per minute; "MPa" means megapascal; "GC" means gas chromatography; "MS" means "mass spectrometry", "Ex" means Example.

Examples 1-4

Examples 1 through 4 demonstrate the conversion of LGone to a first product mixture at 60° C. (Examples 1A, 2A, 3A, and 4A) and the subsequent conversion of the first product mixture to a second product mixture at 180° C. (Examples 1B, 2B, 3B, and 4B), as shown in Reaction Schemes A and B, respectively. In these Examples, the same catalyst was used for the first (A) and second (B) process steps.

Reaction Scheme A

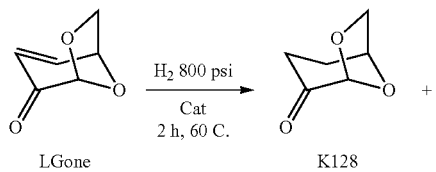

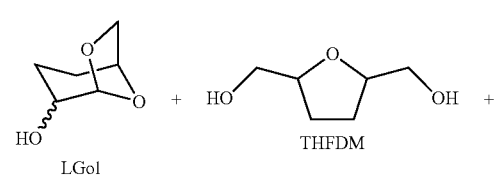

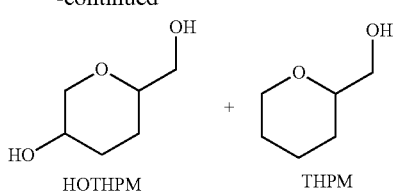

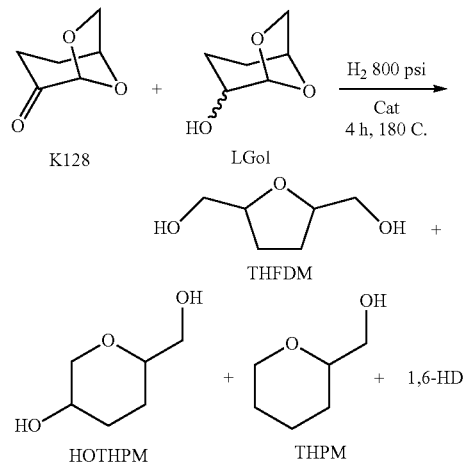

Reaction Scheme B diluted with n-propanol and analyzed by GC and GC/MS. Results for the first reaction products are given in Table 3.

The vials containing the undiluted Step 1 reaction products and catalyst were returned to the reactor, which was then repressurized with 800 psi $H_2$ and allowed to heat to 180° C. After 4 h the reactor was allowed to cool to room temperature within 2 h and depressurized. The second reaction solutions were diluted with n-propanol, filtered through a standard 5 micron disposable filter, and analyzed by GC and GC/MS. Results for the second reactor products are given in Table 3.

TABLE 2

Catalysts and Solvents Used in Examples 1 through 4.

| Example | Process Step | Catalyst | Solvent |
|---------|--------------|----------|---------|
| 1A | First | Pt/C | $H_2O$ |
| 1B | Second | Pt/C | $H_2O$ |
| 2A | First | Pd/C | EtOAc |
| 2B | Second | Pd/C | EtOAc |
| 3A | First | Pd/C | $H_2O$ |
| 3B | Second | Pd/C | $H_2O$ |
| 4A | First | Pd/C | EtOH |
| 4B | Second | Pd/C | EtOH |

TABLE 3

Product Distributions (% mol, based on GC area % corrected using relative response factors) for Examples 1 through 4.

| Ex | LGone | K128 | LGol | THFDM | HOTHPM | THPM | 1,6-HD | 1,2,6-HT |
|----|-------|------|------|-------|--------|------|--------|----------|
| 1A | <1 | 2 | 94 | 3 | 1 | 0 | — | — |
| 1B | <1 | — | <1 | 84 | 7 | 2 | 5 | 1 |
| 2A | <1 | 0 | 95 | 2 | 2 | 1 | — | — |
| 2B | 7 | — | 93 | 2 | 2 | 0 | 3 | 0 |
| 3A | <1 | 0 | 87 | 2 | 3 | 7 | — | — |
| 3B | — | — | 5 | 70 | 20 | 5 | 0 | 0 |
| 4A | <1 | 56 | 42 | 1 | 1 | 0 | — | — |
| 4B | n/a* | n/a | n/a | n/a | n/a | n/a | n/a | n/a |

*"n/a" means not available. The vial containing Example 4B reaction solution broke before the contents could be analyzed.

In a glass vial equipped with a magnetic stir bar (1.5 mL glass vials, ROBO Autosampler Vial, VWR International, Radnor, Pa.), 0.75 ml of solvent (water, ethanol or ethyl acetate [abbreviated as EtOAc]) were added to 37.5 mg of levoglucosenone and about 20 mg of Pt/C or of Pd/C as catalyst as indicated in Table 2 below. The vials were capped with a perforated septum to limit vapor transfer rates. The vials were placed in a stainless steel (SS316) parallel pressure reactor having 8 individual wells. The reactor was connected to a high pressure gas manifold and the contents were purged with nitrogen gas (1000 psi) 3 times. About 800 psi of $H_2$ was then added and the reactor was heated to 60° C. After 2 h the reactor was allowed to cool to room temperature and the pressure was released. Under inert gas atmosphere a 100 μl sample of the first reaction product was taken from each vial, Example 5

Conversion of THFDM to a Product Mixture Comprising 1,6-HD and 1,2,6-HT Using a Pt/W/TiO$_2$ Catalyst at 160° C. and a 6 Hour Reaction Time To a stainless steel (SS316) pressure reactor equipped with a magnetic stir bar and 5 ml of water were added 250 mg of 2,5-tetrahydrofurandimethanol (~95% pure) and about 250 mg of 4% Pt/W/TiO$_2$ catalyst. The reactor was sealed, connected to a high pressure gas manifold, and purged with nitrogen gas (1000 psi) three times. About 800 psi of hydrogen was then added and the reactor was heated to 160° C. After 6 h, the reactor was allowed to cool to room temperature within 2 h and depressurized. The reaction product solution was diluted with n-propanol and a known amount of diethyleneglycoldiethyl ether as an internal standard and filtered through a standard 5 micron disposable filter. A sample was taken and analyzed by GC and GC/MS; results are given in Table 4.

TABLE 4

Results for Example 5

|  | THPM | 1,2-HD | 1,5-HD | 1,5-PD | 1,6-HD | THFDM | 1,2,6-HT | others |
|---|---|---|---|---|---|---|---|---|
| m [mg] | 2 | 2 | 10 | 0 | 132 | 7 | 53 | 6 |
| n [mmol] | 0.01 | 0.02 | 0.09 | 0 | 1.11 | 0.05 | 0.40 | 0.05 |
| Yield | 1% | 1% | 5% | 0% | 62% | — | 22% | 3% |

Example 6

Conversion of THFDM to a Product Mixture Comprising 1,6-HD and 1,2,6-HT Using a Pt/W/TiO$_2$ Catalyst at 160° C. And a 24 Hour Reaction Time Example 6 was conducted the same way as Example 5 but the reaction time was 24 h instead of 6 h. Results are given in Table 5.

TABLE 5

Results for Example 6

|  | THPM | 1,2-HD | 1,5-HD | 1,5-PD | 1,6-HD | THFDM | 1,2,6-HT | others |
|---|---|---|---|---|---|---|---|---|
| m [mg] | 0.8 | 14.0 | 17.0 | 3.2 | 177.0 | 0.0 | 0.0 | ~8.4 |
| n [mmol] | 0.0 | 0.1 | 0.1 | 0.0 | 1.5 | 0.0 | 0.0 | n.d. |
| Yield | 0% | 7% | 4% | 2% | 83% | — | 0% | 4% |

Example 7

Conversion of LGone to a First Product Mixture Comprising LGol at 60° C.

To a stainless steel (SS316) pressure reactor equipped with a magnetic stir bar and 5 ml of water were added 250 mg of levoglucosenone (~90% pure, 10% water) and about 50 mg of 5% Pt/C catalyst. The reactor was sealed, connected to a high pressure gas manifold, and purged with nitrogen gas (1000 psi) three times. About 800 psi of hydrogen was then added and the reactor was heated to 60° C. After 2 h, the temperature was increased to 100° C. over the course of 30 min. After 2 h at 100° C. the reactor was allowed to cool to room temperature within 2 h and depressurized. The reactor was rinsed with water and the reaction product mixture was filtered through a standard 5 micron disposable filter. GC analysis of the filtered product mixture showed quantitative conversion of the levoglucosenone to the corresponding the alcohol levoglucosanol (LGol).

The filtered product mixture of Example 7 was used as the feed solution for Examples 8 through 15, where it is referred to as the "first product mixture".

Example 8 through Example 15

Conversion of a First Product Mixture Comprising LGol to a Second Product Mixture Comprising THFDM and HOTHPM In these Examples, 0.75 ml portions of the filtered product mixture from Example 7, referred to here as the "first product mixture", were placed in each of eight glass vials (1.5 mL glass vials, ROBO Autosampler Vial, VWR International, Radnor, Pa.) together with the amount of catalyst indicated in Table 6. Each portion of the first product mixture contained about 27 mg of LGol. Each vial was equipped with a magnetic stir bar (magnetic stirbar 7×2 mm, VWR International, Radnor, Pa.) and capped with a perforated septum to limit vapor transfer rates. The vials were placed in a stainless steel (SS316) parallel pressure reactor having 8 individual wells. The reactor was connected to a high pressure gas manifold and the contents were purged with nitrogen gas (1000 psi)3 times. About 1200 psi of hydrogen was added while the reaction solutions were stirred. The reactor was then heated to 200° C. and the pressure was adjusted to 2000 psi. After 4 h the reactor was allowed to cool to room temperature within 2 h and depressurized. The second product mixture was diluted with n-propanol and a known amount of diethylene glycol diethyl ether as an internal standard and filtered through a standard 5 micron disposable filter for GC and GC/MS analysis. Results are given in Table 6.

TABLE 6

Results for Examples 8-15

| Ex | Catalyst | Catalyst amount [mg] | Yield mol % | | Other alcohols and unidentified by-products |
|---|---|---|---|---|---|
| | | | THFDM | HOTHPM | |
| 8 | CuO/ZnO | 60 | 38 | 7 | 54 |
| 9 | BaO/CuO/Cr$_2$O$_3$ | 60 | 50 | 7 | 44 |
| 10 | BaO/CuO/MnO$_2$/Cr$_2$O$_3$ | 60 | 51 | 7 | 42 |
| 11 | CuO/SiO$_2$ | 60 | 54 | 8 | 38 |
| 12 | CuO/ZnO/Al$_2$O$_3$ | 60 | 62 | 8 | 30 |
| 13 | CuO/ZnO/CeO$_2$/Al$_2$O$_3$/Na$_2$O/C | 60 | 52 | 5 | 43 |
| 14 | CuO/MnO$_2$/Al$_2$O$_3$ | 60 | 54 | 6 | 40 |
| 15 | 5% Pt/C | 5 | 66 | 10 | 24 |

What is claimed is:

1. A process comprising:
   a) contacting levoglucosenone with hydrogen in the presence of a first hydrogenation catalyst at a first temperature between about 25° C. and about 150° C. to form product mixture (I); and b) heating product mixture (I) in the presence of hydrogen and a second hydrogenation catalyst at a second temperature between about 120° C. and about 260° C. to form product mixture (II).

2. The process of claim 1, wherein product mixture (I) comprises one or more of levoglucosenol, levoglucosanol, tetrahydrofuran 2,5-dimethanol, 2-hydroxymethyltetrahydropyran, 1,2,5,6-tetrahydroxyhexane, 1,2,6-hexanetriol, and 2-hydroxymethyl-5-hydroxytetrahydropyran.

3. The process of claim 1, wherein product mixture (II) comprises one or more of 1,2,6-hexanetriol, tetrahydrofuran 2,5-dimethanol, 2-hydroxymethyl-5-hydroxytetrahydropyran, 1,6-hexanediol, 1,2-hexanediol, 1-hexanol, and 2-hydroxymethyltetrahydropyran.

4. The process of claim 3, wherein product mixture (II) comprises 1,6-hexanediol.

5. The process of claim 1, wherein the first hydrogenation catalyst comprises one or more of supported platinum catalysts, supported palladium catalysts, supported ruthenium catalysts, supported nickel catalysts, catalysts derived from nickel-aluminum alloys, catalysts derived from cobalt-aluminum alloys, and organophosphorous or organometallic complexes of Rh, Ir, Ru, or Ti.

6. The process of claim 1, wherein the second hydrogenation catalyst comprises a metal M1 and optionally a metal M2 or an oxide of M2, and optionally a support, wherein:
M1 is Pd, Pt, or Ir; and M2 is Mo, W, V, Mn, Re, Zr, Ni, Cu, Zn, Cr, Ge, Sn, Ti, Au, or Co; or
M1 is Rh and M2 is Re, Mo, W, V, Mn, Ni, Cu, Zn, Cr, Ge, Sn, Ti, Au, or Zr; or
M1 is Ag, Au or Co; and M2 is Re, Mo, or W;
M1 is Cu, Pd, Fe, or Ni; and M2 is Re, Mo, Cu, Zn, Cr, Ge, Sn, or W; or
M1 is Ag, Pt, Cu, or Au, and M2 is Ni, Fe, Sn, Ge, or Ir; or
M1 is Co and M2 is Fe; or
M1 is Ni and M2 is Co or Fe; or
M1 is Mn and M2 is Cr.

7. The process of claim 1, wherein the second hydrogenation catalyst comprises a catalyst comprising Pt, Cu, Ni, Pd, Rt, Rh, Ir, Ru, or Fe on a $WO_3$ or $WO_x$ support.

8. The process of claim 1, wherein the second hydrogenation catalyst comprises a catalyst comprising metals M1, M2, and M3 and optionally a support, wherein:
M1 is Mn, Cr, V, or Ti; M2 is Ni, Co, or Fe; and M3 is Cu, Ag, Pt, Pd or Au; or
M1 is Pt or Rh; M2 is Cu, Ni or Pd; and M3 is Mo, Re or W.

9. The process of claim 1, wherein the second hydrogenation catalyst comprises a Cu component, optionally a heteropoly acid component; optionally a second metal or metal oxide; optionally one or more promoters; and optionally a support, wherein:
the Cu component comprises Cu or a Cu oxide;
the heteropoly acid component is $H_3[P(W_3O_{10})_4]$, $H_4[Si(W_3O_{10})_4]$, $Cs_{2.5}H_{0.5}[P(W_3O_{10})_4]$; phosphomolybdic acid, or silicomolybdic acid;
the second metal or metal oxide is Cr, a Cr oxide, Ni, a Ni oxide, Mn, a Mn oxide, Zn, or a Zn oxide; and
the one or more promoters are selected from the group consisting of Ba, Ce, Mg, Na, K.

10. The process of claim 1, wherein the second catalyst comprises from 2 weight percent to 98 weight percent CuO, and further comprises from 98 weight percent to 2 weight percent of at least one oxide selected from the group consisting of zinc oxide, magnesium oxide, barium oxide, chromium oxide, silica, alumina, nickel oxide, manganese oxide, sodium oxide, potassium oxide, cerium oxide, lanthanum oxide, iron oxide, silver oxide, and cobalt oxide, based on the total weight of the catalyst.

11. The process of claim 1, wherein the second hydrogenation catalyst comprises $BaO/CuO/Cr_2O_3/SiO_2$, $BaO/CuO/Cr_2O_3$, $BaO/CuO/MnO_2/Cr_2O_3$, $CuO/SiO_2$, $CuO/Al_2O_3$, $CuO/NiO/Al_2O_3$, $CuO/Cr_2O_3/MnO_2$, $CuO/Cr_2O_3$, $CuO/MnO_2/Al_2O_3$, $CuO/Cr_2O_3$, $CuO/SiO_2/Cr_2O_3/MgO$, $CuO/NiO$, or $NiO/CuO/K_2O/Cr_2O_3/CaF_2$.

12. The process of claim 1, wherein steps a) and b) further comprise a solvent, and the solvent comprises water, a $C_1$-$C_{20}$ alcohol, a $C_2$-$C_{20}$ ether, a $C_2$-$C_{20}$ ester, or mixtures thereof.

13. The process of claim 1, wherein the first hydrogenation catalyst comprises Pt/C and the second hydrogenation catalyst comprises $BaO/CuO/MnO_2/Cr_2O_3$.

* * * * *